United States Patent [19]

Eppstein et al.

[11] 4,211,614

[45] Jul. 8, 1980

[54] ENDPOINT DRIFT CORRECTION FOR AUTOMATIC TITRATIONS

[75] Inventors: Lee B. Eppstein, Northport, N.Y.; James K. Kroeger, Glen Ridge, N.J.; Kenneth A. Lindblom, Harrison, N.Y.

[73] Assignee: Photovolt Corporation, New York, N.Y.

[21] Appl. No.: 910,174

[22] Filed: May 30, 1978

[51] Int. Cl.² .......................................... G01N 27/44
[52] U.S. Cl. .................................. 204/1 T; 23/230 R; 204/195 T; 324/425; 364/497; 364/500; 422/75
[58] Field of Search ............. 204/1 T, 195 T; 422/75; 23/230 R; 364/497, 500; 324/29

[56] References Cited

U.S. PATENT DOCUMENTS

| | | | |
|---|---|---|---|
| 3,305,468 | 2/1967 | Liesch | 204/195 T |
| 3,341,430 | 9/1967 | Wickerham et al. | 204/195 T |
| 3,726,778 | 4/1973 | Levy et al. | 204/195 T |
| 3,835,008 | 9/1974 | Fisher et al. | 204/195 T |

Primary Examiner—G. L. Kaplan

[57] ABSTRACT

An apparatus and method are described for automatically correcting drift in automatic titrations, such as coulometric titrations of water. An endpoint detector provides a signal indicative of the state of the titration mixture and the detector signal is monitored by two comparators, responsive to titration mixture states on opposite sides of the endpoint and connected to means for controlling forward and back titration. At the end of a titration, the titration time and amount of titrant are stored in memory elements, and circuitry including an array of gates monitors the comparator signals during two post titration time periods to determine both the direction and rate of drift, and to correct the titration results for the amount of drift detected.

10 Claims, 5 Drawing Figures

ENDPOINT DRIFT CORRECTION FOR AUTOMATIC TITRATIONS

CROSS-REFERENCE TO RELATED APPLICATION

A more detailed description of a filter used in the apparatus of the invention is in a concurrently filed application of James K. Kroeger, Ser. No. 910,173, now abandoned.

BACKGROUND OF THE INVENTION

This invention relates to automatic titrations and titration apparatus, and in a preferred embodiment the invention is concerned with coulometric titration of water using the Karl Fischer reaction with apparatus of the type described in U.S. Pat. No. 3,726,778 to Levy and Seltzer. As described in that patent, such titrations are subject to positive and negative baseline drift, that is, drift away from the endpoint condition not resulting from sample addition. Such drift can be caused by a variety of factors, including side reactions in the titration mixture which either generate or consume the substance being titrated. In coulometric titration of water, aldehyde or ketones in samples will react to produce water. While U.S. Pat. No. 3,726,778 provides one approach to compensation for drift, it would be desirable to provide an apparatus and method adapted for determining accurately the actual amount of drift in each titration and automatically correcting the titration results.

SUMMARY OF THE INVENTION

The invention relates to a method and apparatus for coulometric titration. More particularly, the invention relates to a method and apparatus for accurate and precise determination of the results of a coulometric titration and compensation for drift. In a particularly preferred embodiment the invention concerns an improved method and apparatus for the coulometric titration of water by the Karl Fischer reaction.

As with coulometric titrations generally, the method and apparatus of the invention involve a titration compartment, with means for introducing a titration reagent and sample, an electrolysis anode and cathode in the compartment to pass current through the titration mixture and generate a titrant from the reagent; a detector for determining the condition of the titration mixture relative to a predetermined endpoint; and a source of electrolysis current for the electrolysis electrodes and means for measuring the amount of electric charge passed through the titration mixture. The apparatus can also include additional components, such as an auxiliary electrolysis current source of opposite polarity to the main source for back titration, appropriate filters, buffers, amplifiers and control circuitry to allow the detector to control the titration, display elements for displaying the results in various convenient forms, such as coulombs, titration time, concentration units, etc. The basic structure and use of coulometric titrators is known and conventional. See, for example, Levy and Seltzer, U.S. Pat. No. 3,726,778.

In colulometric titrations, and particularly in coulometric titration of water by the Karl Fischer reaction, the endpoint can be subject to drift, due to a variety of factors such as side reactions, leakage of atmospheric conatminants into the titration compartment, etc. Depending on the chemistry of different samples, drift due to side reactions can vary in both direction and amount, adversely affecting the results of the titration. The invention provides a method and apparatus for compensating for the actual drift occuring during the titration, so that the drift elements in each titration can be accounted for.

In the process of the invention, an electrolysis current is passed through a titration mixture of reagent and sample to generate titrant therein, until the titration mixture first reaches a predetermined endpoint as indicated by an endpoint signal provided by a detector. After the endpoint signal is first reached, electrolysis current is again passed through the mixture whenever the detector signal exceeds the endpoint level, until the mixture is titrated back to the endpoint. The amount of electric charge (Q) used for electrolysis is measured, and the titration time (T) is also measured. After the endpoint condition is reached for the first time, the mixture is monitored and held without measurements being taken for a first predetermined short time period to allow to mixture to stabilize. During this period, the mixing of the titration mixture is continued so that any heterogeneity, due to localized conditions at the titration electrodes or detector electrodes, will be eliminated. Monitoring is then continued for a second, longer time period. If the detector signal does not depart from the endpoint level during the second time period, the amount of sample is determined from the amount of electrolysis current passed through the mixture until the initial endpoint. If, during the second period, the titration mixture departs from the endpoint level the monitoring is continued over a third time interval, beginning with a return to the endpoint condition, continuing for a predetermined time period and ending with another departure from and subsequent retitration to the endpoint condition.

The first post-titration time interval is relatively short, e.g. 5–10 seconds, being only long enough to ensure that localized differences in the titration mixture are eliminated. The second post-titration time interval is generally longer; e.g., 30–60 seconds, when there is no forward or back titration of drift. The predetermined time duration of the second time interval is selected in relation to system time response and titration rate to correspond to, or to exceed the ordinary duration of the initial titration so that absence of forward or back titration during this period will indicate absence of drift during the initial titration. The first period and the predetermined time duration of the second period can be preselected and controlled by a timer. When titratable drift occurs, the end of the second period, and the beginning and end of the third period are in response to the state of the titration mixture. The third time period must begin and end with departures from, or retitrations returning to, the predetermined endpoint condition in order to obtain an accurate determination of the drift rate.

Since the first period is merely to allow stabilization of the titration mixture, the second and third periods are the two time intervals during which drift measurements and corrections occur. In titrations for which no post-endpoint stabilization is required, for example, with rapid mixing and a slow titration rate, the stabilization period can be eliminated.

Electrolysis current passed through the mixture periodically during the third time interval, and the total duration of the third time interval are measured and the average drift rate is determined from the amount of charge used during the third period to maintain the endpoint, and the duration of the third period. The amount of sample titrated is determined from the amount of charge used until the end of the titration adjusted by the drift rate and the measured titration time. Periodically the detector signal is monitored and reverse polarity back titration current is passed through the mixture when the signal reaches a predetermined level beyond the endpoint, and the reverse current is also measured as stated above, and used to determine and adjust for negative drift.

The apparatus of the invention includes conventional elements of a coulometric titrator including electrolysis electrodes, current source, titration compartment, and a detector for detecting the condition of the titration mixture relative to a predetermined endpoint. The detector output signal is connected through a variable low pass filter to a comparator means for comparing the detector output to the predetermined endpoint level. The filter is adapted to vary in response to the comparator between a short time constant condition above the endpoint and a long time constant, high damping condition at or beyond the endpoint. The comparator is also connected to means for controlling the titration current.

The apparatus also includes means for measuring the titration electric charge, and a timer for measuring titration time, and gate means responsive to the time and the comparator for controlling the first post-titration period; second gate means responsive to the first gate means, the timer and comparator for connecting the charge measuring means to output means such as a display when the second post titration time has elapsed without a departure from the endpoint, and for transmitting the measurements of titration time ($T_{titr}$) and titration charge ($Q_{titr}$) at the end of the titration and the time and charge measurements ($T_{co}$ and $Q_{co}$) at the beginning of the third post-titration period to first and second memory means; third gate means responsive to the second gate means, the timer and the comparator for transmitting the measurements of titration electric charge ($Q_{cl}$) and time ($T_{cl}$) from the measuring means and timer when the selected retitration occurs at the end of the third time period; means responsive to the third gate means and connected to the and second memory means for generating a signal corresponding to ($Q_{cl} - Q_{co}/T_{cl} - T_{co}$), which thus corresponds to the average drift rate (D.R.) during the third time interval; multiplier means connected to the subtractor/divider means and the first reader/memory means for generating a signal corresponding to the amount of drift taking place during the titration, (D.R.$\times T_{titr} = Q_{titr}$); and adder and subtractor means connected to the first reader/memory and the multiplier means for connecting the titration result $Q_{titr}$ by subtracting or adding the amount of electric charge $Q_{corr}$ attributable to titration of positive or negative drift.

The titration time measured in the process and apparatus of the invention is the total of (a) a relatively brief sample introduction period (during which the sample to be titrated is introduced into the titration reagent), (b) the time between the end of the sample introduction period and beginning of titrant introduction by switching on the main electrolysis current source; and (c) the time during which titration current is passed through the mixture until the endpoint condition is first reached. Period (a) is a relatively brief period, e.g. 5-10 seconds to allow time for the introduction of sample. Period (b) can be eliminated, however, it is preferred in the case of certain samples to allow a delay of 10 to as long as 3600 seconds, to permit complete mixing, or extraction of materials from solid samples into the titration mixture. This can be provided by including a convention delay timer to delay operation of the current source for selected times. Since drift due to side reactions, atmospheric contamination, etc. can occur during periods (a) and (b), it is necessary to include such periods in the titration time.

DETAILED DESCRIPTION

Figure 4:
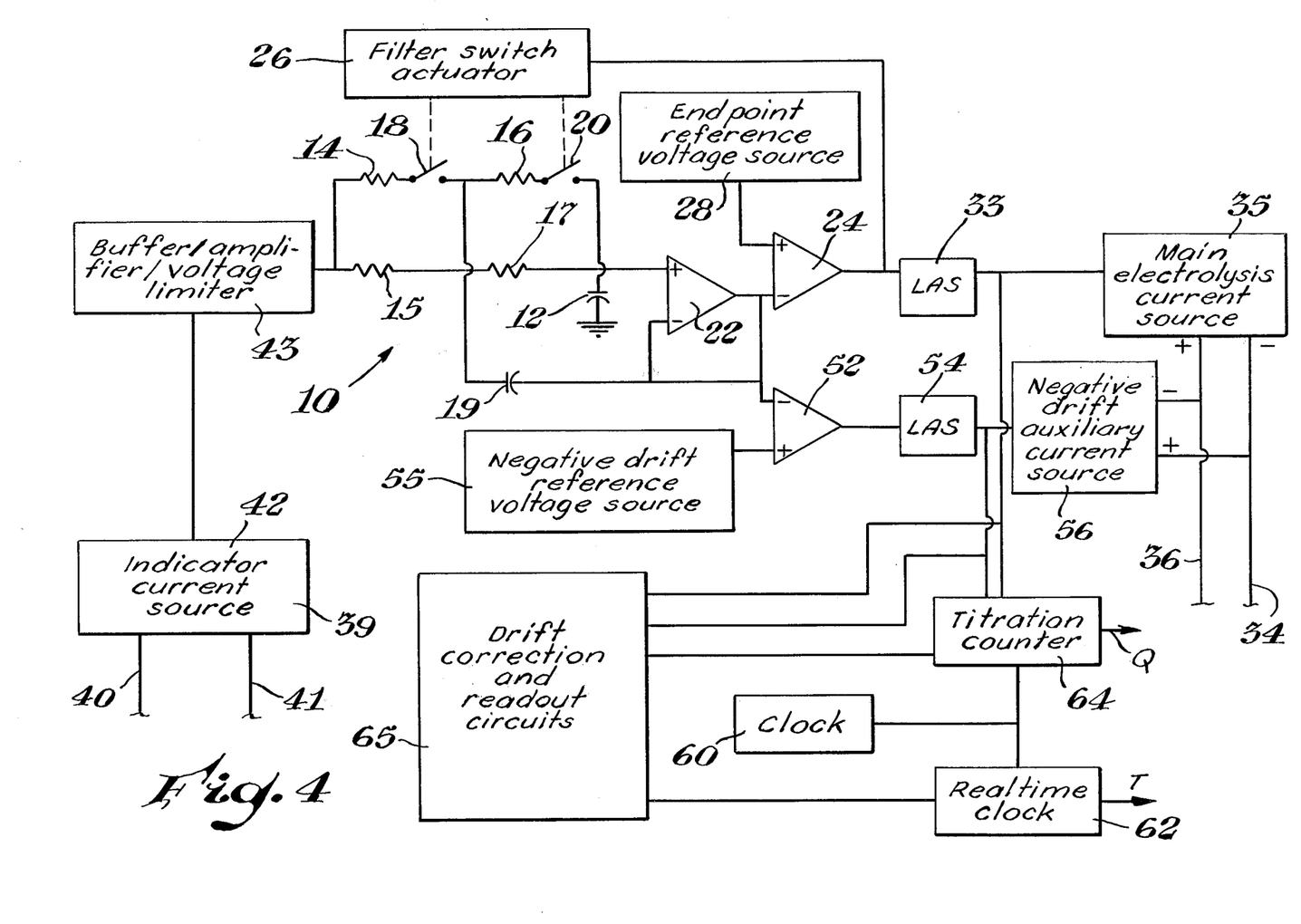
FIG. 4 is a block diagram illustrating the operating and control circuits of a titrator of the invention.
Figure 5:
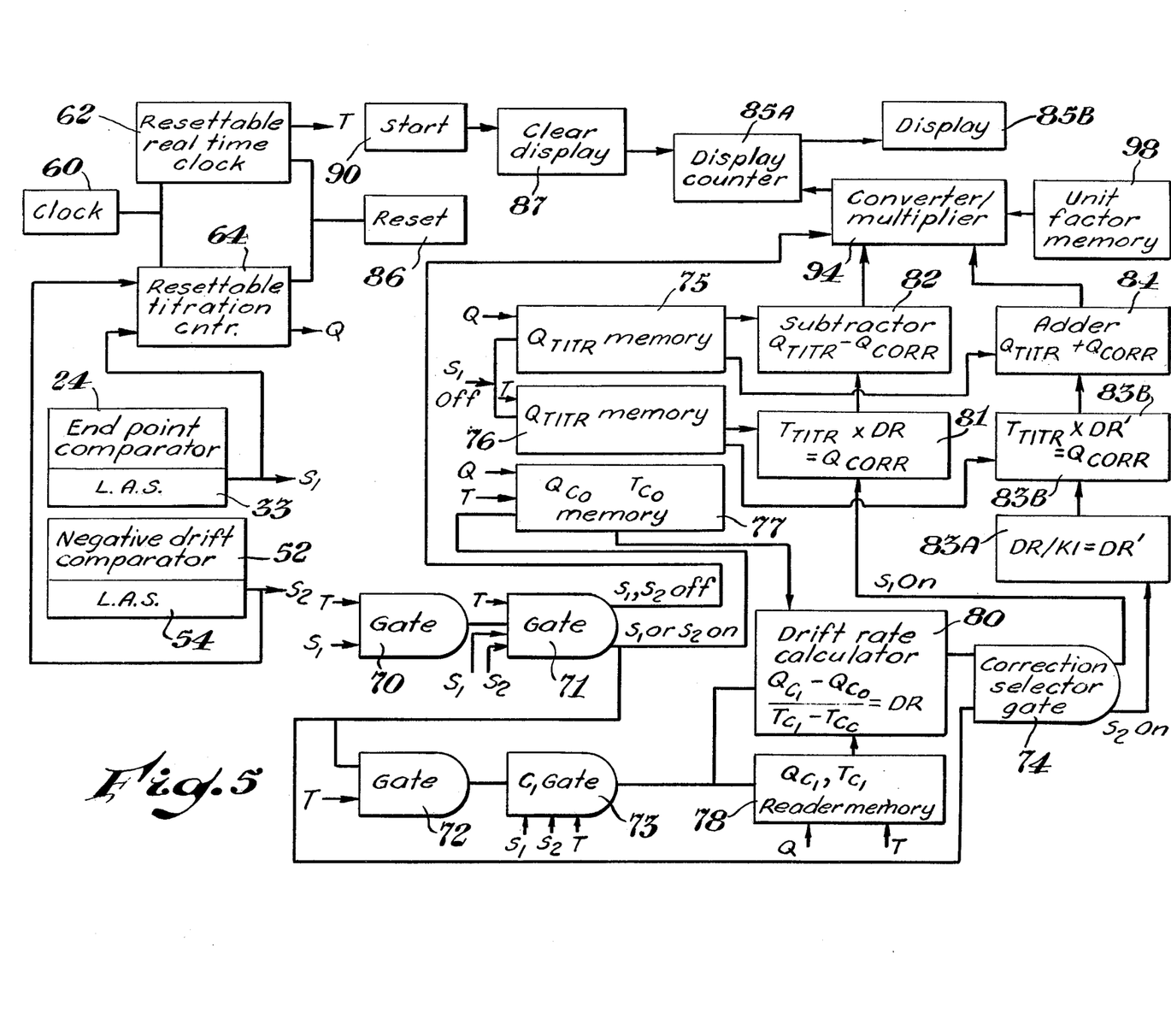
FIG. 5 illustrates details of the measurement and drift correction circuits of a titrator of the invention in an embodimemt adapted for coulometric Karl Fischer titrations.

As illustrated in the embodiments of FIGS. 4 and 5, the apparatus comprises electrolysis electrodes 34, 36 connected to a main electrolysis current source 35, and an endpoint detector 39, including electrometric sensing electrodes 40, 41, and indicator current source 42. A negative drift auxiliary current source 56 is also provided, connected to electrodes 34, 36 with opposite polarity to main current source 35. These basic elements are conventional and described, for example, in U.S. Pat. No. 3,726,778 in reference to Karl Fischer titrators.

Figure 2:
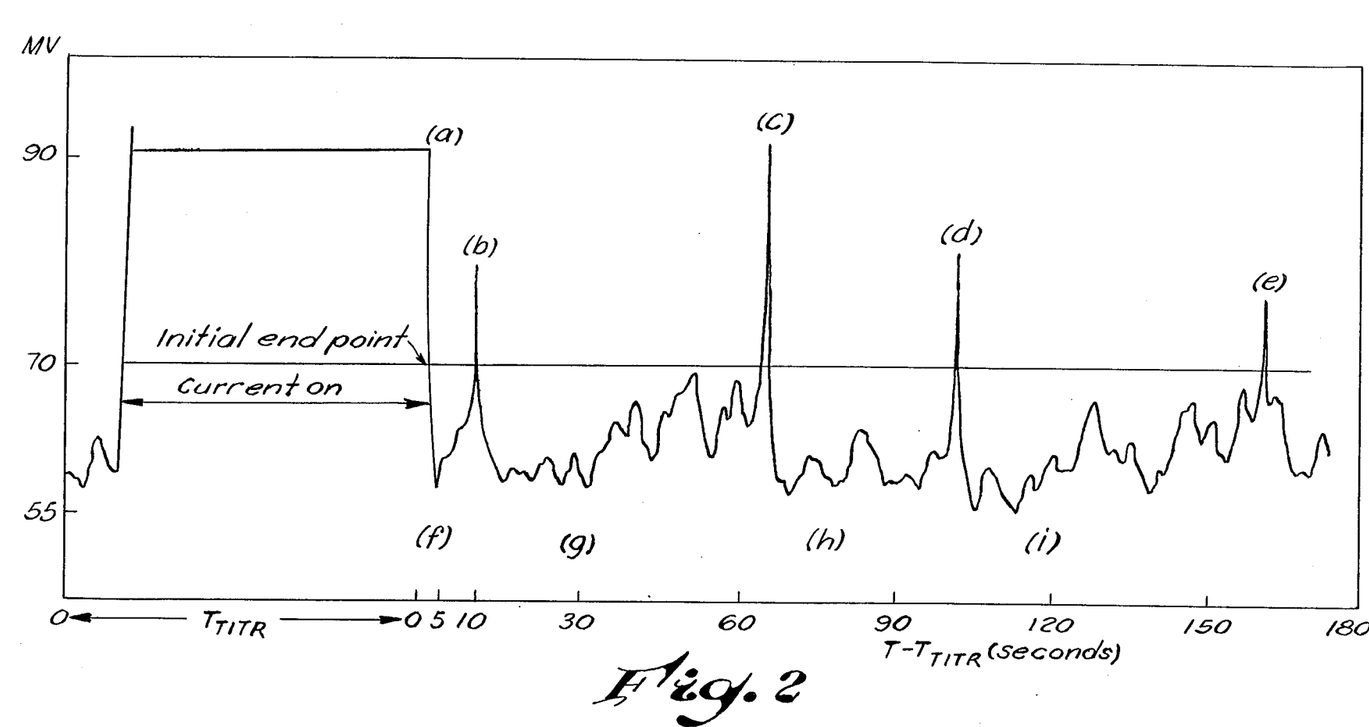
FIG. 2 illustrates the filtered detector output signal in a titration exhibiting relatively slow positive drift.
Figure 3:
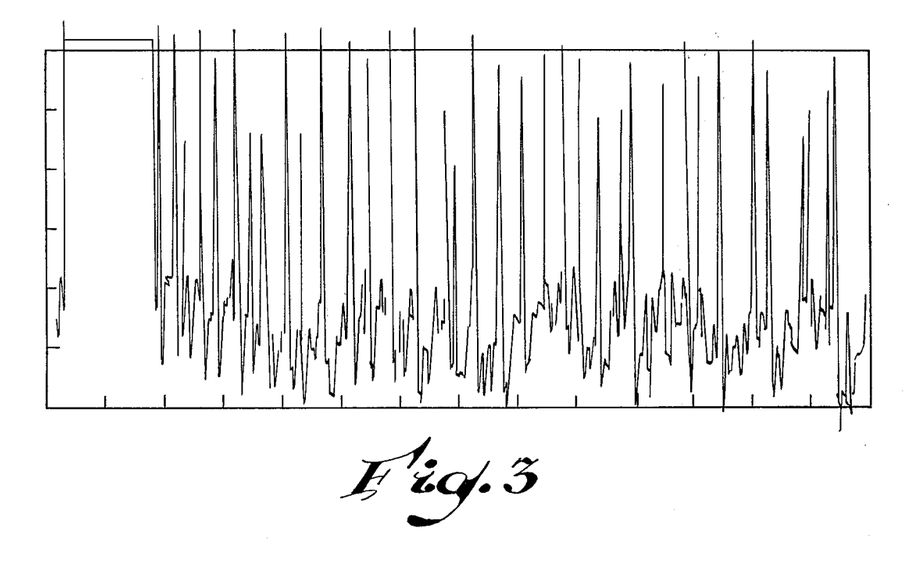
FIG. 3 illustrates the filtered detector output signal in a first titration exhibiting relatively high positive drift.

Endpoint detector 39 is connected through conventional buffer and voltage limiter circuits 43 to a variable low pass filter 10, and the output of filter 10 (the filtered detector signal) is connected to endpoint comparator 24 and negative drift comparator 52. A predetermined endpoint reference voltage source 28 is connected to endpoint comparator 24 to provide a reference voltage corresponding to the titration endpoint. The output signal of comparator 24 (indicated as S, in FIG. 5) is connected to a light actuated switch, LAS 33, which controls the operation of the main current source 35 while electrically isolating the comparator 24 from current source 35 and titration counter and drift correction circuitry 60, 62, 64, 65. In a coulometric Karl Fischer titrator embodiment with an amperometric sensing electrode as detector 39, the detector signal is voltage, which decreases during the titration as water is consumed, to an endpoint value of, for example, about 70 millivolts. Comparator 24 and LAS 33 are connected to activate electrolysis current source 35 when the signal from detector 39 indicates the presence of untitrated sample and to switch off current source 35 when the detector signal reaches the endpoint reference level provided by voltage source 28. The current source 35 remains switched off at LAS 33 until the detector signal at comparator 24 returns to the endpoint level (due to drift, untitrated sample, new sample addition, etc.). As best shown in FIGS. 2 and 3, the electrolysis current source 35 will be activated periodically after the endpoint is first reached.

Figure 1:
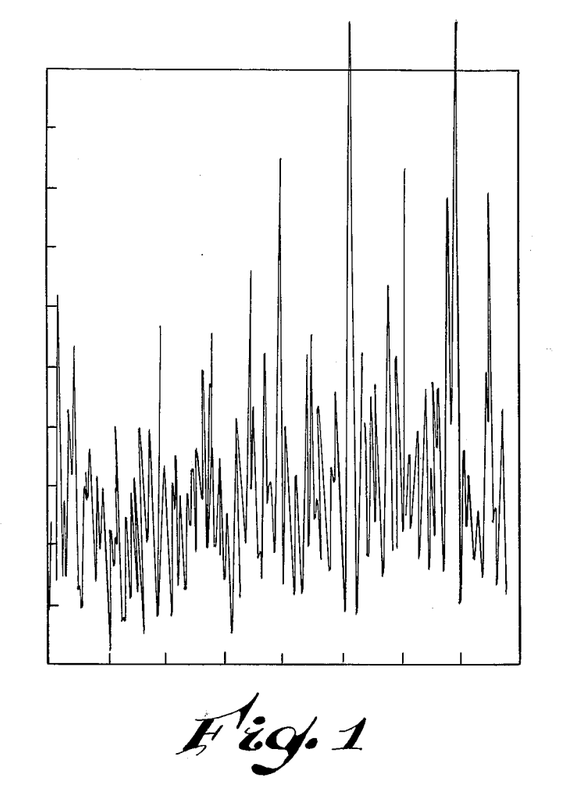
FIG. 1 illustrates the unfiltered detector output signal from the endpoint detector of a coulometric Karl Fischer titrator illustrative of the invention.

As illustrated in FIG. 1, the unfiltered output from detector 39 is an extremely noisy signal. The filtered signals of FIGS. 2 and 3 illustrate more typical titrations. As best shown in FIG. 2, a titration continues for an initial titration time $T_{titr}$, beginning with the start of a sample introduction period, continuing through a period during which the constant current source operates, and ending when the titration reaches its initial endpoint, at $T-T_{titr}=0$ in FIG. 2. (The signal illustrated is voltage limited to a maximum shown at (a) in FIG. 2.) Although the electrolysis current is switched off at the endpoint, at $T-T_{titr}=0$, the detector signal exceeds the endpoint, to (f) then begins to return during an initial post titration stabilization period. The second post titration period ends and the third period begins at $T-T_{titr}=10$ seconds, when the titration current is switched on and off, giving rise to a retitration "spike" (b). With the retitration at (b), the signal again goes beyond the endpoint, then gradually drifts upward at (g) during the third time period. The upward drift is followed by another retitration spike (c), an "overshoot" and upward drift (h) to another retitration spike (d). With a third time period having a minimum time duration of, for example, 30 to 50 seconds, the third time period would be 55 seconds long, from the beginning of spike (b) at $T-T_{titr}=10$ seconds to the beginning of spike (c) at $T=65$ seconds. With a minimum third period duration of 60 seconds, the third period would continue until the beginning of spike (d) at $T-T_{titr}=102$ seconds, making the third period 92 seconds long (from $T-T_{titr}=10$ to $T-T_{titr}=102$).

As best shown in FIG. 2, the drift cycles, (f), (g), (h), and (i) are not uniform in duration. It is necessary for the third time period to begin and end with a post titration spikes, preferably with the beginnings of spikes. The third time periods in different titrations, will not necessarily be of the same duration.

To provide a quick shut off of titration current at the endpoint, together with adequate filtering of the detector signal so that return to the endpoint can be reliably detected, filter 10 comprises capacitor 12, connected in series through resistors 15, 17 to the detector input, and connected to amplifier 22. Two additional resistors 14, 16 are switchably connected in parallel with one of resistors 15, 17 via switches 18, 20. Switches 18, 20 (both shown open in FIG. 4 are controlled by actuator 26 connected to the output of comparator 24, so that both the switches 18, 20 are closed or both switches are opened substantially simultaneously. Resistors 14, 16 are selected to provide different resistances in the RC filter circuit, and thus different cut off frequencies and time constants depending on whether resistors 14 and 16 are switched into or out of the circuit. Switch actuator 26 is connected to comparator 24 to provide short-time-constant/high-pass filtering during the titration and long-time-constant/low-pass filter characteristics when the endpoint is met or exceeded. Further details of the filter 10 are described in a copending commonly assigned application, concurrently filed herewith by James K. Kroeger, Ser. No. 910,173, hereby incorporated by reference.

As shown in FIG. 4 the filtered detector signal is also connected a negative drift comparator 52, which is also connected to a reference voltage source 55. This reference voltage is a predetermined level corresponding to negative drift of the detector signal below the endpoint level. For example, in Karl Fischer titrator with an endpoint reference of 70 millivolts, a suitable negative drift reference level can be 55 millivolts. Comparator 52 is connected to an LAS 54 which switches the negative drift auxiliary current source on or off, in response to the output signal $S_2$ of comparator 52.

The outputs of comparators 24, 52 are connected through the respective light activated switches 33, 54 to a resettable titration counter 64, which measures the electric charge used to titrate or to correct drift, and to a drift correction/readout circuit 65. When both current sources 35, 56 are constant current sources, for example, the main electrolysis source preferably provides +100.35 milliamperes when switched on, and negative drift source 56 provides −25.09 milliamperes. With constant current electrolysis, titration counter 64 is preferably a clock or timer, which records the time during which the current sources operate. A clock 60 is connected to both titration counter 64 and real time clock 62 to provide uniform timing measurement.

DRIFT CORRECTOR AND READOUT 65

As shown in FIG. 5, main titration comparator 24 through LAS 33 provides a signal $S_1$, which corresponds to the endpoint status of the detector signal and the main electrolysis current from source 35. Similarly, a signal $S_2$ from comparator 52 and its LAS 54 indicates the negative drift status of the detector signal and negative drift correction current source 56. Titration counter 64 provides a signal Q, which corresponds to electric charge used in titration, the signal Q being a measurement of the time that either current source 35 or source 56 has been switched on. Clock 62 provides a signal T, which corresponds to the actual duration of the titration procedure independently of switching on and off of sources 35 and 56 before and after the endpoint is first reached.

For simplicity, signals $S_1$, $S_2$, T and Q are shown repeatedly as inputs or connections to various elements in FIG. 5. It is understood that the apparatus includes appropriate connections between the comparators 24, 52, LAS 33 and LAS 54, counter 64 and clock 62 to supply these signals.

The drift corrector and readout circuits 65, include a series of gate systems (gates 70, 71, 73, 74); reader/memory elements 75, 76, 77, 78 for signals T and Q at various times controlled by clock 62 and comparators 24, 52 through the gates 70, 71 72 and 73; signal function manipulators (80, 81, 82, 83, 84) connected to certain of the reader/memory elements 75, 76, 77, 78 and gate 74 and a readout circuit 85. The readout circuit 85 includes conventional display apparatus for displaying the results, recorder, etc., and associated conventional apparatus, e.g. converter 94 for converting the results to a desired numerical units, such as coulombs, moles, millimoles, micrograms, etc. and desired numerical base, such as binary, octal, decimal, etc. Such apparatus is well known and the particular type of readout apparatus is not critical.

A reset element 86 is connected to clock 62 and counter 64 to reset the clock and counter and clear the memories when a start signal from a start switch 90 is produced.

The gates, reader/memory elements, and function manipulators 70–84, follow the titration and any post titration drift, correct the result for drift (if any) and transmit the final result to the readout 85. When the readout 85 receives the final result, reset element 86 resets the titration counter 64 and clock 62. In a further embodiment, the device includes additional circuits to monitor drift periodically in the apparatus between titrations, and to apply the most recent drift correction to the readout during subsequent titrations until the first endpoint.

The apparatus is controlled at several points by signals $S_1$ and $S_2$ from comparators 24, 52. Each comparator signal corresponds to one of two states of the detector signal and current sources 35, 56. For brevity, the two signal states are hereinafter referred to as OFF and ON, corresponding to the following;

$S_1$ = OFF, detector signal below endpoint, main titration current source 35 off;

$S_1$ = ON, detector signal at or above endpoint, main titration current source on;

$S_2$ = OFF, detector signal above predetermined negative drift limit (which is below the endpoint level); auxiliary current source off; and $S_2$ = ON, detector signal below negative drift limit; auxiliary current source on.

OPERATION

A titration is started, e.g., by actuating a "start" switch 90 just prior to adding a sample to the titration reagent, clearing the display and actuating reset element 86. Reset element 86 resets and starts the clock 62, and resets counter 64 to zero, and briefly inhibits operation of the current source 35 for a predetermined sample introduction period. If the sample contains water detected by indicator 39, $S_1$ goes to the ON state, and starts counter 64. When the titration first reaches the endpoint, the signal $S_1$ from comparator 24 goes to OFF, stopping the titration counter 64 but not the clock 62; and T and Q are transferred to memory elements 75, 76. These signals are $T_{titr}$ (titration time) and $Q_{titr}$ (titration charge). The "5-second" gate 70 follows the signal T from clock 62 for 5 seconds after $S_1$ first goes to OFF, then activates the "30-second" gate 71. The 30 second gate monitors the clock signal T, and $S_1$ and $S_2$. If both $S_1$ and $S_2$ remain OFF for the entire period, gate 71 transmits the signal $Q_{titr}$ from memory 75, through subtractor 82 to the display 85 and converter/multiplier 94. $S_1$ and $S_2$ both remain OFF only if there is no detectable drift during this period, therefore $Q_{corr}$ in subtractor 82 is zero.

In the usual case, some drift will occur and either $S_1$ or $S_2$ will switch ON during the period controlled by gate 71, as the device either titrates positive drift back to the endpoint or back titrates negative drift back to the pre-set limit. When either $S_1$ or $S_2$ goes to ON during this period, the 30 second gate transmits the clock 62 and counter 64 signals T and Q to memory elements 77. T and Q at this time can be designated as $T_{Co}$, and $E_{Co}$ the subscript "Co" denoting the beginning of the drift correction measurements. Gate 71 also activates gate 72, and, in response to which comparator signal ($S_1$ or $S_2$) is ON, activates correction selector gate 74 to connect function elements 81, 82 for $S_1$=ON or function elements 83, 84 for $S_2$=ON.

Once activated by $S_1$ or $S_2$ going to ON, the 45 second gate monitors the time signal T from clock 62 and then activates the $C_1$ Gate 73 after 45 seconds. The activated $C_1$ Gate monitors $T_1$, $S_1$ and $S_2$, and when either $S_1$ or $S_2$ goes to ON again, or if neither $S_1$ or $S_2$ go ON for 30 seconds gate 73 transfers Q and T at that time to $Q_{C1}$, $T_{C1}$ reader/memory element 78. The subscript "$C_1$" denotes the end of the correction measurement period.

The apparatus has thus determined the titration charge $Q_{titr}$ and time $T_{titr}$ until $S_1$ first reached OFF; delayed 5 seconds; then monitored $S_1$ and $S_2$ during a second time interval, and determined T and Q at the beginning ($T_{Co}$, $Q_{Co}$) and end ($T_{C1}$, $Q_{C1}$) of a third time interval which started with $S_1$ or $S_2$ switching On after the 5 second delay and ended with the next ON state of $S_1$ or $S_2$ which occured after the expiration of 45 seconds from the start of the third time interval or, if there is no subsequent ON state within the 30 seconds of the $C_1$ gate 73, which ended after the 45 seconds of gate 72 plus the 30 seconds of gate 73.

Gate 73 also activates the drift rate calculator function element 80, which uses $Q_{Co}$ and $T_{Co}$ from memory 77 and $Q_{C1}$ and $T_{C1}$ from reader/memory element 78 to generate a drift rate signal corresponding to:

$$(Q_{C1} - Q_{Co}/T_{C1} - T_{Co})$$

Element 80 thus comprises subtractors and a divider element.

If $S_1$ was ON during the post titration period, correction selector gate 74 transmits the drift rate signal from calculator 80 to correction multiplier 81 which multiplies the drift rate signal by $T_{titr}$ stored in memory element 76 to produce a drift correction value signal $Q_{corr}$, corresponding to the amount of titration charge $Q_{corr}$ which was consumed during the titration by drift compensation rather than by titrating sample water. $Q_{corr}$ is transmitted from multiplier 81 to subtractor 82, which receives $Q_{titr}$ from memory 75. Subtractor 82 subtracts $Q_{corr}$ from $Q_{titr}$ and transmits the resulting signal, now corresponding to the titration result corrected for drift ($Q_{titr} - Q_{corr}$), to display 85 via converter/multiplier 94.

If negative drift occured, $S_2$ was ON during the post titration period. Gate 74 transmits the drift rate from calculator element 80 to correction multipliers 83, A and B which multiply the drift rate by $T_{titr}$ (83B) and divide (83A) by a factor $K_1$ corresponding to the ratio of main titration current to negative drift auxiliary current. E.g. when the main current is 100.35 ma and the auxiliary current is $-25.09$ ma, the drift rate from calculator 80 must be reduced by a factor of 4, since $Q_{C1} - Q_{Co}$ is actually only a measurement of time, not current. The resulting correction value $Q_{corr}$ corresponds to the amount of additional charge which would have been used in the titration if negative drift had not occurred. Multiplier 83 transmits $Q_{corr}$ to adder 84 which adds $Q_{corr}$ to $Q_{titr}$ (transferred from memory 75) and transmits the resulting signal to the readout 85.

It will be apparent from the foregoing that the corrected result signal from either subtractor 82 or adder 84 (or from counter 64 via gate 71 when there is no drift) is a measurement of titration charge in terms of titration time at constant titration current. The display element 85 preferably includes a conventional converter/multipliers 94 and unit factor memory 98 to convert the corrected Q to coulombs, or to moles, or micrograms of water or other desired units.

In an alternative embodiment of the invention the display elements 85 can be supplied with a partially corrected Q signal during the titration and before the drift correction process is completed. This allows the operator to observe approximate results as the titration progresses, so that unusual conditions, such as sample addition errors, etc. can be signalled early. This can be done for example, by providing an additional memory element (not shown) to store the most recently determined drift rate DR (or DR/$K_1$ in case of negative drift) and correcting the Q display using the most recent drift rate correction.

The invention has particular applicability in coulometric titration of water by the Karl Fischer reaction, in apparatus of the type described by Levy and Seltzer in U.S. Pat. No. 3,732,778, the disclosure of which is hereby incorporated by reference. Such apparatus includes electrolysis electrodes 34, 36 in contact with the titration mixture for passing current through the mixture to generate iodine which is consumed in the Karl Fischer reaction, and indicator or detector electrodes 40, 41 in contact with the reaction mixture for detecting the endpoint of the titration electrometrically. The amount of electric charge required by the electrolysis electrodes in order to reach the endpoint state is measured to give a measurement of water titrated. By using a constant electrolysis current, the coulometric measurement can utilize a timer. Coulometric water titrators of this type are described in the above U.S. Pat. No. 3,726,778, and are commercially available, e.g., Aquatest II Karl Fischer Titrator, Photovolt Corporation, New York, N.Y..

In such an apparatus, the signal from the detector is inherently a rather noisy signal. With conventional filtering methods the signal-to-noise ratio is improved by using a long time-constant RC filter system, but the titration control is delayed, which can allow the titration to progress beyond the endpoint. Back titration must then be employed. In addition baseline drift frequently occurs after titration of sample water is complete, necessitating both positive and negative stabilization.

DISPLAY OF RESULTS

The interaction of the drift correction circuits, drift monitor circuitry and display 85 is illustrated in FIG. 5.

As shown in FIG. 5, readout 85 comprises a digital display panel 85b controlled by a counter 85a. The result signals $Q_{titr}+Q_{corr}$, $Q_{titr}-Q_{corr}$ or $Q_{titr}$, from the adder 84 or subtractor 82 are, as noted above, in units corresponding to time at constant current. A convertor/multiplier 94 is provided to multiply the Q signals by the appropriate conversion factor (from a conversion factor memory 95) so that the display 85b is in desired units such as micrograms of water. In construction and operation the titration counter may be counting time at a much higher rate than is desired for the display counter. (E.g., if clocks 60 and 62 and titration counter 64 are counting at 600 Hertz, it may be desirable to have the display counter operate at 1 hertz or less, particularly when it is desired to display Q during the titration.) Converter/multiplier 94 thus can use two conversion factors, a display factor to convert titration counter time units to display counter time units, and a second conversion factor proportional to the main electrolysis current (coulombs/time) to provide a display in units such as coulombs, moles, micrograms of water, etc.

When it is desired to display a corrected Q value continuously during the titration, the apparatus can be modified to provide an additional memory element (not shown) to store the drift rate (DR, or DR' for negative drift) from the most recent titration, and multiplier elements to continuously apply that drift rate factor to the Q signal to be displayed. If desired, a drift correction factor used for continuous Q displays can be revised periodically between titrations by resetting clock 62 and counter 64, and clearing memory elements 75, 76, 77, 78 at the end of a titration correction sequence, and using the gates 70, 71, 72, 73, 74, memories 77 and 78 and element 80 to monitor drift conditions between titrations. Such modifications add to the complexity of the apparatus and method, and do not improve accuracy, since the drift rate correction employed for continuous Q display is ultimately revised by the correction process after the actual titration is completed.

Elements 70–84, 94 and 98 can be assembled using separate integrated circuit chips, e.g., gates, memories, adders, subtractors, multipliers, etc., or preferably using a conventional arithmetic logic unit for the arithmetic operations. Preferably, these elements as well as clocks 60, 62 and counter 64 are memory locations in a microprocessor. Commercially available units such as an Intel microprocessor No. 8085, with two programmable read-only memory units (Intel No. 2716) and a random access memory (Intel No. 8156), Intel Corp., Santa Clara, California are used in a preferred apparatus. It will be apparent, also, that the $Q_{titr}$ memory 75, $T_{titr}$ memory 76, and $Q_{Co}$ and $T_{Co}$ and $Q_{C1}$, $T_{C1}$ memory elements 77 and 78 can be constructed using separate display elements, or an appropriate printer, to provide the necessary values of $Q_{titr}$, $T_{titr}$, $Q_{Co}$, $T_{Co}$, $Q_1$ and $C_1$, so that the correct computations can be carried out separately, either manually or on a separate, appropriately programmed digital computer, for example. Also the time periods applied by the various gates 70, 71, 72, and 73 can be varied.

The invention has been described with respect to coulometric Karl Fischer titration of water, with an endpoint condition sensed as voltage and approached during the titration from a higher endpoint detector voltage so that positive drift corresponds to increasing voltage and negative drift corresponds to negative voltage. It will be apparent, however, that the method and apparatus can be readily adapted to other titrations and other endpoint detection systems, such as, for example, the system described by Dahms in U.S. Pat. No. 3,723,062.

An apparatus of the type described was constructed using a 100.35 milliampere titration current, a −25.09 ma negative drift titration current, and a 70 millivolt endpoint in a general construction as disclosed in the above-mentioned patent to Levy and Seltzer and the application of Kroeger, with the above-mentioned Intel microprocessor and memory components, using a 5 second stabilization period at gate 70, a 30 second period for gate 71, a 45 second period at gate 72 and a 30 second period for gate 73. In representative titrations of a sample containing 450 micrograms of water, with no drift, the mean result was 450 micrograms with a standard deviation of ±5. With a 450 microgram sample and positive drift (due to acetone in the sample) of about 300 micrograms/minute, the mean result corrected by the invention was 468 micrograms with a standard deviation of ±13. The uncorrected mean result was 745 ±18. In a similar operation with moderate drift, the uncorrected mean $Q_{titr}$ of replicate samples containing 608 ±8.9 micrograms water was 2200 micrograms, while the apparatus and method of the invention gave a mean corrected result of 575 micrograms with a standard deviation of ±25.6 micrograms. It will be apparent that the invention not only provides improved results in coulometric titrations, but allows coulometric titrations under drift conditions in which coulometric titration was previously impractical.

What is claimed is:

1. In an automatic titrator comprising titration means for introducing a titrant into a titration mixture, endpoint detection means for detecting the endpoint of the titration, means responsive to the endpoint detection means for controlling the titration means to introduce titrant when the titration mixture is not at the endpoint, and titrant measuring means for measuring the amount of titrant introduced, the improvement which comprises;

(a) timer means for measuring the titration time until the titration mixture first reaches an initial endpoint, (b) means responsive to one of the endpoint detection means and the titration means for detecting introduction of titrant during a predetermined post-titration time period after the initial endpoint;

(c) means for measuring the amount of titrant introduced during a subsequent post-titration time period after the initial endpoint, said subsequent time period beginning with the detection of titrant introduction by means (b), and ending with a predetermined subsequent introduction of titrant; and (d) means including a timer for measuring the duration of said subsequent post-titration period, said time and amount measurements by means (c) and (d) being indicative of the drift rate during the titration, and the drift rate and the titration time measured by means (a) being indicative of the amount of drift.

2. A titrator of claim 1 wherein the titrator is a coulometric titrator, the titration means includes electrolysis electrodes and a constant current source for electrolytic generation of titrant in the titration mixture, and the titrant measuring means includes a timer responsive to the current source for measuring the duration of electrolytic generation of titrant, and generating a titration measurement signal Q, and the timer means (a) includes a clock means for generating a time signal T and wherein the improvement further comprises:

(e) gate means responsive to one of the endpoint detection means and the current source and to the time signal T for detecting operation of the current source during a predetermined post-titration period;

(f) display means responsive to gate means (e) for displaying the titration measurement signal Q when the gate means detects expiration of the time period without operation of the current source;

(g) gate means responsive to gate means (e) and to the time signal T for determining the minimum predetermined duration of the second post-titration period, beginning with detection of current source operation, being also responsive to the endpoint detection means for determining the end of the second post-titration period;

(h) memory means responsive to the endpoint detection means for storing the titration measurement signal $Q_{titr}$ and the time signal $T_{titr}$ at the initial endpoint;

(i) second and third memory means for determining the time and titration measurement signals, $T_{Co}$ and $Q_{Co}$ at the beginning, and $T_{C1}$ and $Q_{C1}$ at the end, of the second post-titration period.

3. In a coulometric titrator having electrolysis electrodes for electrolytically generating titrant in a titration mixture, a constant current source for providing electrolysis current to said electrodes, and an endpoint indicator for providing an endpoint signal indicative of the status of the titration mixture relative to the endpoint of the titration, the improvement which comprises:

a clock for generating a time signal T during and after a titration;

a titration counter for generating a charge signal Q corresponding to the charge passed through the titration mixture by the electrodes and constant current source;

a comparator connected to the endpoint detector and adapted to provide a signal $S_1$ having an $S_1 = ON$ state when the endpoint signal is above a predetermined endpoint level and an $S_1 = OFF$ state when the endpoint signal is at or below the endpoint level;

means including a switch responsive to the comparator signal $S_1$ for activating the current source and the titration counter when $S_1 = ON$ and inactivating said source and counter when $S_1 = OFF$;

first gate means responsive to the time signal T and comparator signal $S_1$ for detecting a recurrence of the $S_1 = ON$ state during a predetermined time period after $S_1$ first attains the $S_1 = OFF$ state at the end of a titration;

memory means responsive to signals $S_1$, T and Q, including a titration time memory and a titration charge memory for storing T and Q signals, $T_{titr}$ and $Q_{titr}$, when $S_1$ first attains the $S_1 = OFF$ state at the end of a titration;

display means for displaying the signal Q as a titration result $Q_{titr}$ in response to the first gate means signal corresponding to the lapse of the first gate time interval without a recurrence of $S_1$ attaining the $S_1 = ON$ state;

drift correction memory means responsive to signals T and Q and the first gate means, for storing the T and Q signal as $Q_{Co}$ and $T_{Co}$ in response to the first gate signal indicative of occurrence of the $S_1 = ON$ state during the first gate time interval;

drift correction means including second and third gates, the second gate being responsive to the first gate and the time signal T to activate the third gate at a predetermined time after the first gate signal indicative of occurrence of the $S_1 = ON$ state during the first gate time interval, and the third gate being responsive to the $S_1$ signal and the second gate;

second drift correction memory means responsive to the Q and T signals and to the third gate means for storing the Q and T signals as $Q_{C1}$ and $T_{C1}$ at the time the third gate indicates occurence of the $S_1 = ON$ state of signal $S_1$.

4. The device of claim 3 further comprising dirft rate calculator means responsive to the third gate for generating a drift rate signal DR from the Q and T signals in the first and second drift correction memory means, the signal DR corresponding to $$Q_{C1} - Q_{Co}/T_{C1} - T_{Co}.$$

5. The device of claim 4, further comprising multiplier means for providing a result correction signal $Q_{corr}$ from the titration time signal $T_{titr}$ in the first memory means and the drift rate signal DR, $Q_{corr}$ being the product of $T_{titr} \times DR$;

a subtractor for subtracting the $Q_{corr}$ signal from the $Q_{titr}$ signal in the first memory means; and means for transmitting the difference from said subtraction to the display means to display the corrected result.

6. The device of claim 5, further comprising a negative drift constant current source of opposite polarity to the electrolysis current source;
- a second comparator connected to the endpoint detector and adapted to provide a signal $S_2$ having an $S_2=$ON state when the endpoint signal is below the endpoint by a predetermined amount and an $S_2=$OFF state when the endpoint signal is above said predetermined amount;
- means for switching the negative drift current source ON and OFF in response to the second comparator signal $S_2$ being ON or OFF; and
- wherein the first and third gate means and first and second drift correction memory means are adapted to operate the same when either $S_1$ or $S_2$ is in the ON state;
- the device further comprising means including a correction selector gate responsive to the first gate means for indicating which of $S_1$ and $S_2$ attains the ON state during the first gate time interval.

7. A method for correcting positive drift in a titration or a titration mixture, comprising
- generating a signal Q corresponding to the amount of titrant introduced into the titration mixture;
- generating a time signal T corresponding to time elapsed from beginning of the titration;
- introducing titrant continuously until a predetermined endpoint condition is detected, and thereafter reintroducing titrant periodically as needed to maintain the reaction mixture at the endpoint condition;
- storing the Q and T signals as $Q_{titr}$ and $T_{titr}$ at the time the endpoint is first reached;
- when no additional titrant is introduced during a predetermined time interval after the endpoint is first reached, determining the titration result from $Q_{titr}$; and
- when additional titrant is introduced during said interval, generating a drift rate signal DR corresponding to the difference between (i) the Q signal at the time $T_{Co}$ of an additional titrant introduction ($Q_{Co}$) and the Q signal at the time $T_{C1}$ of a predetermined later additional titrant introduction ($Q_{C1}$) divided by (ii) the difference in time ($T_{C1}-T_{Co}$) between said introductions;
- generating a correction signal $Q_{corr}$ corresponding to the product of the drift rate signal DR and the stored $T_{titr}$ signal, said correction signal thus corresponding to the amount of titrant consumed by drift during the initial titration; and
- determining the titration result from the difference between the stored $T_{titr}$ signal and the $T_{corr}$ signal.

8. Method of claim 7 wherein the titration is a coulometric titration, and titrant is introduced by passing a constant current through the titration mixture to generate titrant electrolytically, and wherein the introduction of titrant is controlled by providing an endpoint detection signal, $S_1$, having a first state $S_1=$ON when the titration mixture is above or at a predetermined endpoint, and a second state $S_1=$OFF when the titration mixture is below the endpoint, and switching the constant current source ON when $S_1=$ON and OFF when $S_1=$OFF.

9. Method of claim 8 wherein the signal Q is generated by generating a time signal while the $S_1$ signal is in the $S_1=$ON state, whereby the signal Q corresponds to the time during which the constant current source is ON.

10. Method of claim 9 wherein the first predetermined time interval is commenced a sufficient time after the endpoint is first reached for the titration mixture to become substantially homogenous.

* * * * *